US012527965B2

(12) United States Patent
Winek et al.

(10) Patent No.: US 12,527,965 B2
(45) Date of Patent: Jan. 20, 2026

(54) EXTENDABLE AND RETRACTABLE LEAD

(71) Applicant: Medtronic, Inc., Minneapolis, MN (US)

(72) Inventors: Michael E. Winek, Minneapolis, MN (US); Lauren E. Barth, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 812 days.

(21) Appl. No.: 17/505,320

(22) Filed: Oct. 19, 2021

(65) Prior Publication Data

US 2022/0118262 A1 Apr. 21, 2022

Related U.S. Application Data

(60) Provisional application No. 63/198,469, filed on Oct. 21, 2020.

(51) Int. Cl.
*A61N 1/375* (2006.01)
*A61N 1/36* (2006.01)

(52) U.S. Cl.
CPC ......... *A61N 1/375* (2013.01); *A61N 1/36067* (2013.01); *A61N 1/36096* (2013.01)

(58) Field of Classification Search
CPC ................ A61N 1/375; A61N 1/36067; A61N 1/36096; A61N 1/0551
See application file for complete search history.

(56) References Cited

U.S. PATENT DOCUMENTS

| | | | | |
|---|---|---|---|---|
| 4,614,395 | A * | 9/1986 | Peers-Trevarton | H01R 11/24 439/389 |
| 8,543,222 | B1 * | 9/2013 | Sochor | A61B 90/11 607/116 |
| 2019/0060642 | A1 * | 2/2019 | Boggs, II | A61N 1/0558 |

OTHER PUBLICATIONS

Oscor, "Physique Extendable/Retractable Active Fixation Lead". Sep. 2013, as available at https://pdf.medicalexpo.com/pdf/oscor/physique-extendable-retractable-active-fixation-lead/96411-129786.html, 2 pgs.

* cited by examiner

*Primary Examiner* — Carl H Layno
*Assistant Examiner* — Aya Ziad Bakkar
(74) *Attorney, Agent, or Firm* — Husch Blackwell LLP

(57) ABSTRACT

An extendable and retractable electrical lead for providing electrical stimulation including an elongated lead body extending from a proximal portion to a distal portion, one or more electrical contacts carried by the proximal portion of the lead body configured to be coupled to an implantable neurostimulator, one or more electrodes carried by the distal portion of the lead body configured to electrically communicate with the one or more electrical contacts to deliver neurostimulation therapy to a target treatment site based on a stimulation therapy provided by an implantable neurostimulator; and a protective sheath coaxially aligned with the lead body along a common axis and extending over part of a length of the lead body, where the protective sheath is configured to slide relative to the lead body and the common axis between an extended state and a retracted state.

14 Claims, 5 Drawing Sheets

EXTENDABLE AND RETRACTABLE LEAD

CROSS-REFERENCE TO RELATED APPLICATIONS

This application claims the benefit of U.S. Provisional Application Ser. No. 63/198,469, filed Oct. 21, 2020, the disclosure of which is hereby incorporated by reference in its entirety.

FIELD

The present technology is generally related to implantable neurostimulation devices and more particularly to electrical leads affiliated with such devices.

BACKGROUND

Treatments using neurostimulation systems have become increasingly common in recent years. Neurostimulation (also referred to as neuromodulation) has been used to treat a variety of ailments and associated symptoms including acute pain disorders, movement disorders, affective disorders, as well as bladder related dysfunction.

Examples of pain disorders that may be treated by neurostimulation include failed back surgery syndrome, reflex sympathetic dystrophy or complex regional pain syndrome, causalgia, arachnoiditis, and peripheral neuropathy. Movement disorders include muscle paralysis, tremor, dystonia and Parkinson's disease. Affective disorders include depressions, obsessive-compulsive disorder, cluster headache, Tourette syndrome and certain types of chronic pain. Bladder related dysfunctions include overactive bladder ("OAB"), urge incontinence, urgency-frequency, and urinary retention. OAB can include urge incontinence and urgency-frequency alone or in combination. Urge incontinence is the involuntary loss of urine associated with a sudden, strong desire to void (urgency). Urgency-frequency is the frequent, often uncontrollable urges to urinate (urgency) that often result in voiding in very small amounts (frequency). Urinary retention is the inability to empty the bladder.

Neurostimulation treatments can be configured to address a particular condition by effecting neurostimulation of targeted nerve tissues relating to the sensory or motor control associated with that condition or associated symptoms. Neurostimulation devices typically include an implanted neurostimulator such as an implantable pulse generator (IPG) coupled to an electrical lead that includes one or more electrodes positioned near the distal end of the lead.

In various examples, it may be necessary to reposition the placement of the distal end of the electrical lead. For example, during implantation, the implanted location of the electrodes may be sub optimal requiring repositioning. Additionally, or alternatively, at the completion of electrical lead's intended lifespan, it may be desirable to remove and replace the lead with a new lead. The distal end of such electrical leads can often be the most delicate and the stresses exerted on lead during such repositioning or extraction procedures, particularly when the manipulation of the lead occurs at the proximal end of the lead, tissue has built up around the lead, or both, can cause the lead to malfunction, fracture, or become separated. Such setbacks may require more invasive action by the clinician to resolve any of these challenges. In some examples, these potential drawbacks may cause the clinician to leave the obsolete lead implanted within the patient rather than risk its removal and introduce a new lead alongside the obsolete lead.

The disclosed electrical leads may address one or more of these challenges by providing an electrical lead with a retractable and extendable distal segment.

SUMMARY

The techniques of this disclosure generally relate to an extendable and/or retractable electrical lead for an implantable neurostimulation device. The retractable leads include an elongated lead body having a distal portion that includes at least one electrode and an outer protective sheath configured to move relative to the lead body along a common axis so that the distal portion of the lead body can be withdrawn coaxially within the protective sheath to provide protection to the delicate features of the lead body during implantation and extraction of the lead.

In one aspect, the present disclosure provides an extendable and retractable electrical lead for providing electrical stimulation including an elongated lead body extending from a proximal portion to a distal portion, one or more electrical contacts carried by the proximal portion of the lead body configured to be coupled to an implantable neurostimulator, one or more electrodes carried by the distal portion of the lead body configured to electrically communicate with the one or more electrical contacts to deliver neurostimulation therapy to a target treatment site based on a stimulation therapy provided by an implantable neurostimulator; and a protective sheath coaxially aligned with the lead body along a common axis and extending over part of a length of the lead body, where the protective sheath is configured to slide relative to the lead body and the common axis between an extended state and a retracted state.

In another aspect, the present disclosure provides a method of producing the extendable and retractable electrical lead as disclosed and described herein.

In another aspect, the present disclosure provides a method of protecting a distal end of an electrical lead. The method includes providing the extendable and retractable electrical lead as described herein in a retracted state, the distal end of the extendable and retractable electrical lead being positioned adjacent to a target treatment site; and transitioning the extendable and retractable electrical lead to the extended state while keeping the protective sheath substantially stationary relative to the target treatment site.

In another aspect, the present disclosure provides a method of manufacturing an extendable and retractable electrical lead, the method comprising forming an elongated lead body having a proximal portion and a distal portion, forming at least one electrical contact on the proximal portion of the elongated lead body, wherein the proximal portion of the elongated lead body is configured to be coupleable to an implantable neurostimulator device. The method further includes forming at least one electrode on the distal portion of the elongated lead body, coupling the at least one electrical contact to the at least one electrode such that the at least one electrode is configured to deliver neurostimulation therapy to a target treatment site based on a stimulation therapy provided by the implantable neurostimulator device, forming a protective sheath, and joining the protective sheath and the elongated lead body such that the protective sheath is coaxially aligned with the lead body along a common axis and extending over part of a length of the lead body, wherein the protective sheath is configured to be slidable relative to the lead body and the common axis between an extended state and a retracted state.

In another aspect, the present disclosure provides an extendable and retractable electrical lead for providing electrical stimulation comprising an elongated lead body extending from a proximal portion to a distal portion, one or more electrical contacts carried by the proximal portion of the lead body and configured to be coupled to an implantable neurostimulator, one or more electrodes carried by the distal portion of the lead body configured to electrically communicate with the one or more electrical contacts to deliver neurostimulation therapy to a target treatment site based on a stimulation therapy provided by an implantable neurostimulator, and a protective sheath coaxially aligned with the lead body along a common axis and extending over part of a length of the lead body, the protective sheath including an elongated tubular section and at least one flexible seal coupled to a distal end of the tubular section, wherein the protective sheath is configured to be slidable relative to the lead body and the common axis between an extended state and a retracted state, further wherein in the retracted state, the tubular section is positioned over the one or more electrodes, the tubular section is proximal to the one or more electrical contacts and not positioned over the one or more electrical contacts, and the second end of the flexible seal is positioned proximal relative to the first end, and in the extended state, the second end of the flexible seal is positioned distal relative to the first end and the tubular section is proximal to the one or more electrical contacts and not positioned over the one or more electrical contacts, and wherein the protective sheath and the lead body are configured to transition between the retracted state and the extended state by manipulating the protective sheath and the lead body at the proximal portion of the retractable electrical lead.

The details of one or more aspects of the disclosure are set forth in the accompanying drawings and the description below. Other features, objects, and advantages of the techniques described in this disclosure will be apparent from the description and drawings, and from the claims.

Figure 1:
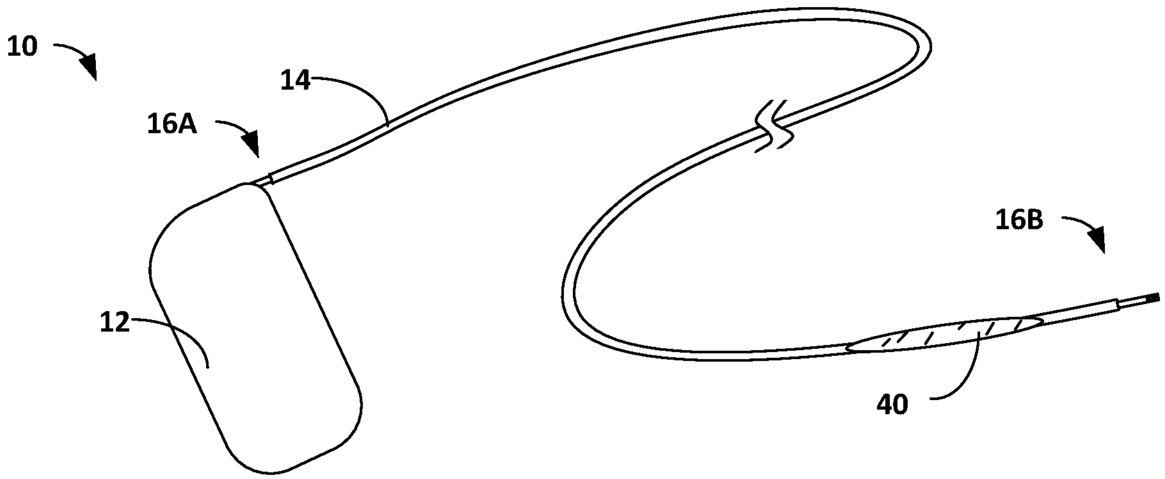
FIG. 1 is schematic illustration of an example nerve stimulation system that includes an implantable neurostimulation device coupled to an extendable and/or retractable electrical lead.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Neurostimulation devices typically include an implanted neurostimulator such as an implantable pulse generator (IPG) coupled to an electrical lead that includes one or more electrodes positioned near the distal end of the lead. During implantation, the distal end of the lead may be navigated through the interior of a patient's body with the distal end implanted at a target treatment site for the receipt of neurostimulation. Such locations may include within the cardiovascular system of the patient, near the bladder or sacral nerve, within brain tissue, near the spinal cord, or the like.

FIG. 1 is a schematic view of an example neurostimulation system 10 that includes an implantable neurostimulator 12 and a retractable electrical lead 14. Electrical lead 14 can include a flexible, elongated body that extends from a proximal end 16A to distal end 16B. Proximal end 16A of retractable electrical lead 14 is configured to be secured and electrically coupled to neurostimulator 12, and distal end 16B is configured to be implanted at a target treatment location within a patient to provide neurostimulation therapy.

Figure 2A:
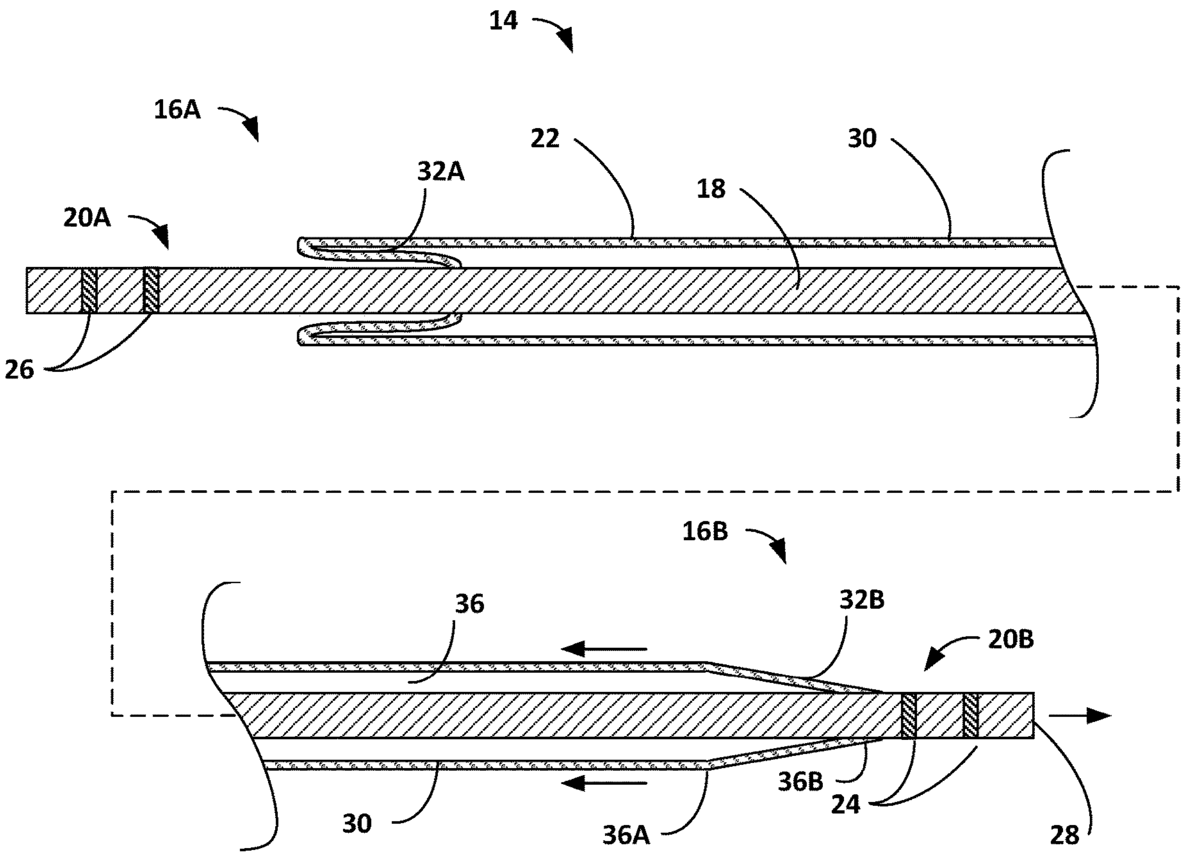
FIG. 2A is schematic illustration of an example extendable and/or retractable electrical lead in an extended state that can be used with the nerve stimulation system of FIG. 1.
Figure 2B:
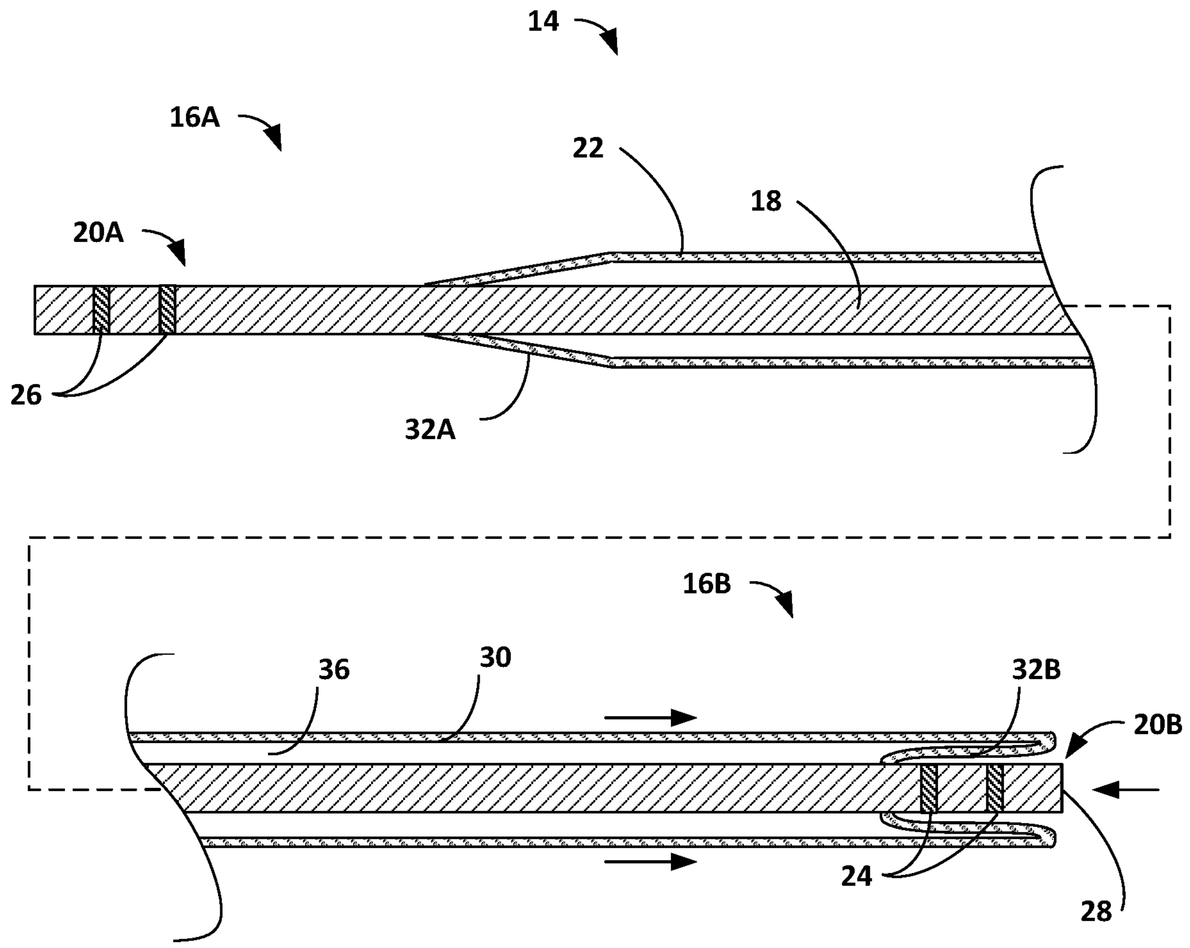
FIG. 2B is schematic illustration of the extendable and/or retractable electrical lead of FIG. 2A in retracted state.

FIGS. 2A and 2B are schematic cross-sectional views of retractable electrical lead 14 in an extended and retracted state respectively. Retractable electrical lead 14 can include an inner lead body 18 having a proximal portion 20A and distal portion 20B. Electrical lead 14 can also include a protective sheath 22 aligned coaxially with lead body 18 so that protective sheath 22 partially extends over lead body 18.

Distal portion 20B of lead body 18 can include one or more electrodes 24 configured to deliver electrical neurostimulation therapy to a target treatment site and proximal portion 20A can include one or more electrical contacts 26 configured to directly electrically couple to neurostimulation device 12. Electrical contacts 26 are electrically coupled to electrodes 24 through lead body 18 to deliver the electrical signal from neurostimulation device 12 therebetween. Such coupling can occur through one or more electrical wires, coils, conductors, or the like. In other embodiments, one or more electrodes 24 may be disposed along the length of electrical lead 14, in addition to or instead of electrodes on a distal portion of the lead.

Protective sheath 22 can extend coaxially over a portion of lead body 18. In embodiments, protective sheath 22 can extend coaxially over less than about half of lead body 18, over about half of lead body 18, over more than about half of lead body 18, over a substantial portion of lead body 18, or over nearly the entirety of lead body 18. Protective sheath 22 and lead body 18 are configured to transition between the extended state (FIG. 2A) and retracted state (FIG. 2B). For example, lead body 18 and protective sheath 22 are configured to move relative to one another along a common axis (e.g., the shared coaxial axis).

In the extended state (FIG. 2A) distal end 28 of lead body 18 is extended distally from protective sheath 22 as indicated by the arrows in FIG. 2A. In the extended state, both proximal and distal portions 20A and 20B of lead body 18 are exposed allowing for direct coupling between electrical contacts 26 and neurostimulation device 12 and for direct tissue contact between electrodes 22 and the target treatment site.

The extended state may be considered as the implanted or normal state by which retractable electrical lead 14 is to be implanted within the patient. In the extended state, lead 14 is configured to function as intended to deliver neurostimulation to a target treatment site using one or more of electrodes 24. In the extended state, protective sheath 22 is not intended to interfere with or otherwise impede the functionality of neurostimulation system 10.

In the retracted state (FIG. 2B), distal portion 20B of lead body 18 is withdrawn relative to protective sheath 22 so that the distal end 28 of lead body 18 is pulled toward the inner lumen of protective sheath 22 as indicated by the arrows in FIG. 2B. In the retracted state, the otherwise delicate and sensitive components of distal portion 20B of lead body 18 are surrounded and protected by the more robust structure of protective sheath 22. While in the retracted state, distal portion 16B of electrical lead 14 may be repositioned as needed followed by deployment or redeployment of distal portion 20B of lead body 18 into a desired target tissue or location. Additionally, or alternatively, electrical lead 14 may be fully extracted from the patient while in the retracted state.

Protective sheath 22 may be configured to be stronger and more robust to axial forces as compared to lead body 18 allowing for the easy maneuvering or extraction of electrical lead 14 without damaging distal portion 20B of lead body 18. Further, because inner lead body 18 moves coaxially relative to the outer protective sheath 22, only a relatively small distal portion of lead body 18 is brought into contact with and moves relative to the patient tissue while the protective sheath remains otherwise fixed relative to the patient tissue. Thus, only the relatively small distal portion of lead body 18 is stressed by the contact with patient tissue and is less apt to malfunction, fracture, or separate during repositioning or extraction. Because protective sheath 22 is configured to be more robust to axial strain compared to the inner portion of the lead body 18 alone, lead 14 can be conveniently and reliably extracted from the patient once with distal portion 20B the lead body 18 secured within protective sheath 22.

While protective sheath 22 and lead body 18 are configured to move relative to one another, in practice it may be preferable to maintain protective sheath 22 in a stationary position relative to the patient while transitioning lead body 18 between the extended and retracted states. By doing so, only distal 20B of lead body 18 may be moving relative to the patient which can reduce the axial strain and forces on lead body 18 compared to a traditional lead that does not include protective sheath 22.

Electrical contacts 26 are exposed while in the retracted and extended states, which allows the clinician to connect proximal end 20A of lead body 18 to neurostimulation device 12 during implantation or maneuvering of electrical lead 14 so that the placement of electrodes 24 within the target tissue site may be interrogated while still allowing lead 14 to be transitioned to a retracted state and/or manipulated if the placement of electrodes 24 needs further adjustment.

In some embodiments, protective sheath 22 may include a non-expandable tubular section 30 and a flexible seal 32A/32B at the distal end or at both the distal and proximal ends of tubular section 30. Tubular section 30 may comprise a robust polymer such as silicone, polyester, polyurethane. Optionally, tubular section 30 may include one or more reinforcement materials such coils, wires, braids, multiple laminated layers, plurality of segmented tubular sections of different stiffnesses, or other design features to improve the strength of tubular section 30.

Flexible seal 32A/32B may include any flexible polymeric material capable of folding back on itself so that flexible seal 32A/32B can be drawn into the inner lumen 34 of protective sheath 22 when lead 14 is extended into either a retracted state (e.g., for a distal flexible seal 32B) or extended state (e.g., for a proximal flexible seal 32A). Suitable materials may include, but are not limited to silicone, polyester, polyurethane, or the like.

Referencing the distal flexible seal 32B, the seal may have a first end 36A bonded to the distal end of tubular section 30 and a second end 32B bonded to lead body 18 to prevent fluid from entering the inner lumen of tubular section 30. Preventing body fluids from entering inner lumen 36 may help ensure smooth relative movement between lead body 18 and protective sheath 22 even after implantation for an extended period of time. In some embodiments, the first and second ends of flexible seal 32B may be bonded to the indicated portions of tubular section 30 or lead body 18.

The depiction of lumen 36 in FIGS. 2A and 2B are meant purely for illustrative purposes. In some embodiments, lumen 36 may be sized to be substantially the same as the outer diameter of lead body 28. Additionally, in some embodiments the inner surface of tubular section 30, the surface of lead body brought into contact with tubular section 30, or both may include a lubricious coating, surface treatment, or similarly effective material surfaces, that reduces friction between the surfaces to allow for smooth relative movement of the lead body 18 and protective sheath 22.

In some embodiments, the extension and retraction of lead body 18 may be actuated by the physical manipulation of electrical lead 14 by the clinician near proximal portion 20A. Additionally, or alternatively, the transition between extended and retracted states of electrical lead may be actuated by actuating wires or hydraulic injection that can be manipulated by the clinician at the proximal end or at an intermediary access point of lead 14 manually or with the aid of a tool.

The number of electrodes 24 and electrical contacts 26 may be selected to correspond with the type of neurostimulator 12 electrical lead 14 is coupled to. Neurostimulator 12 may include any suitable neurostimulator device and is not intended to be limiting. In some embodiments, lead 14 may include two electrodes 24 and corresponding electrical contacts 26, or lead 14 may include four electrodes 24 and corresponding electrical contacts 26, or any desired number of electrodes 24 and corresponding electrical contacts 26.

Retractable electrical lead 14 may optionally include one or more anchoring devices 40. Anchoring device 40 may be connected to protective sheath 22 and used to secure electrical lead 14 relative to the tissue of the patient to prevent inadvertent movement of electrical lead 14 while implanted within the patient. Anchoring device 40 may include one or more structural features such as barbs, protrusions, and the like that help physically retain electrical lead 14 within the patient's tissue. Additionally, or alternatively, anchoring device 40 may include one or more suture points or a suturable material that can be used to suture anchoring device 40 to the patient's tissue. Anchoring device 40 may be positioned along electrical lead 14 at a position proximal of distal portion 20B of lead body 18 the anchoring device 40 does not interfere with the operation of electrical lead 14.

Figure 3A:
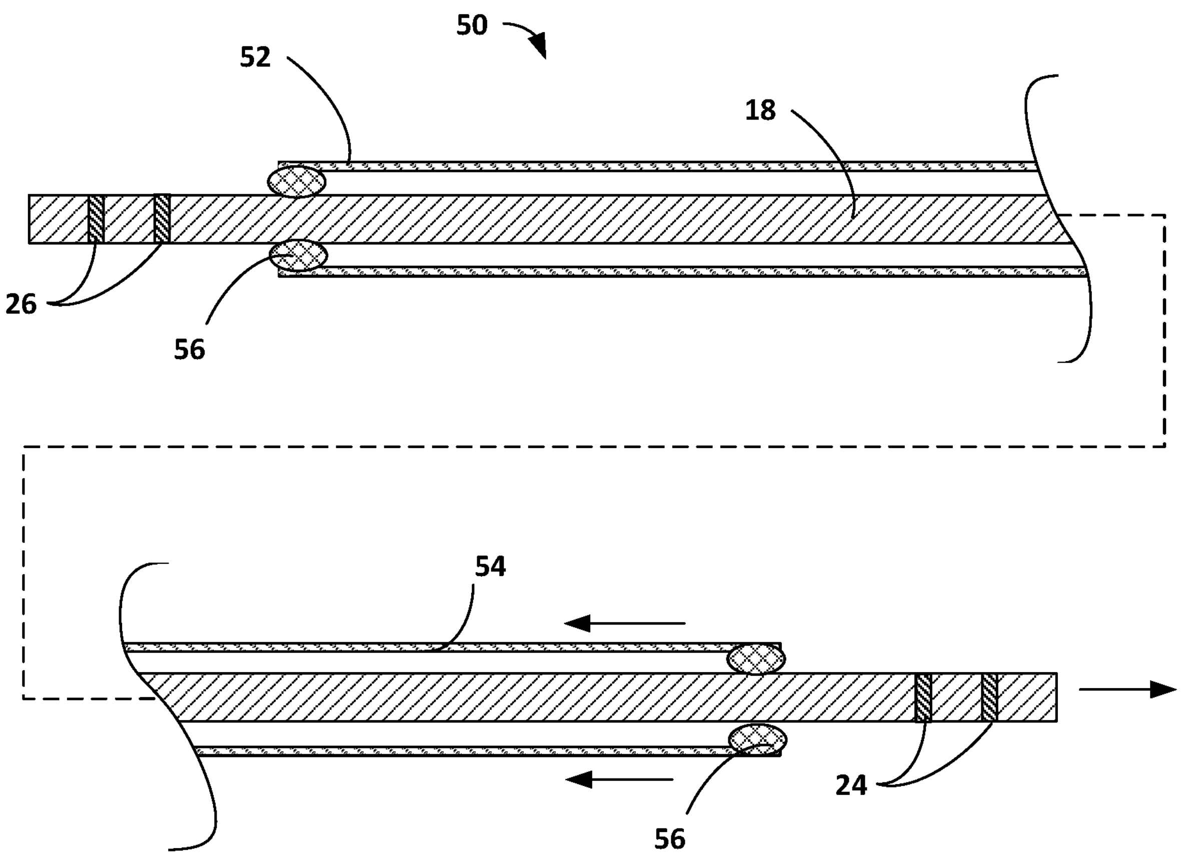
FIG. 3A is schematic illustration of another example extendable and/or retractable electrical lead in an extended state that can be used with the nerve stimulation system of FIG. 1.
Figure 3B:
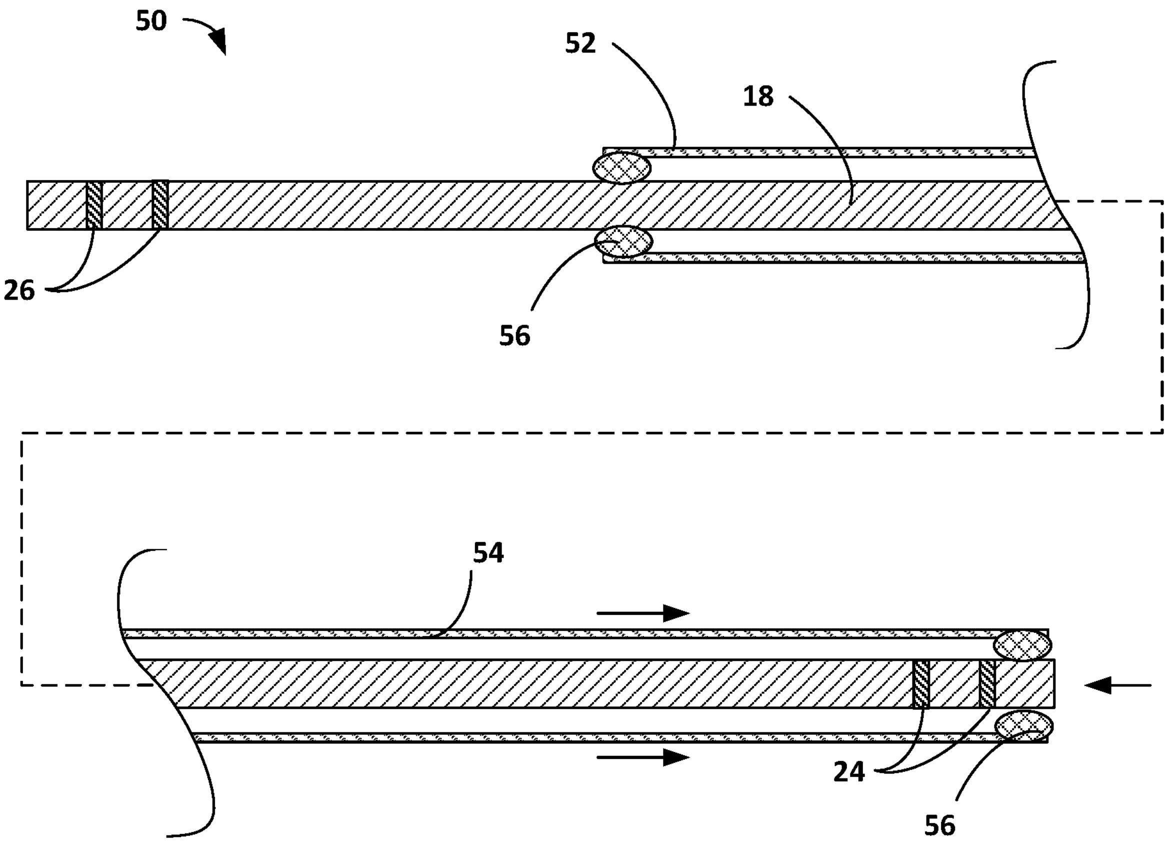
FIG. 3B is schematic illustration of the extendable and/or retractable electrical lead of FIG. 3A in retracted state.

FIGS. 3A and 3B are a schematic cross-sectional views of another retractable electrical lead 50 in extended and retracted states respectively that can be used with the neurostimulator system 10 of FIG. 1. Electrical lead 50 includes lead body 18, which may be substantially similar to lead body 18 of FIGS. 2A and 2B, and protective sheath 52. Protective sheath 52 includes a tubular portion 54 and sliding gasket 56 positioned at the proximal and distal portions of tubular portion 54. Sliding gasket 56 may be configured to permit the axial movement of protective sheath 52 relative to lead body 18 to transition electrical lead 50 from a retracted state to an extended state as shown by the arrows in FIGS. 3A and 3B.

Tubular portion 54 may be constructed using one or more of the materials described above with respect to sheath 22. Sliding gaskets 56 may resemble an o-ring and constructed using similar materials to flexible seal 32A/32B. In some embodiments, gaskets 56 may be bonded or fixed relative to tubular portion 54.

In some embodiments, electrical leads 14 may also include expandable or compressible sections to account for the relative movement of the tip, visible or radiopaque markers to visualize relative movement and location of lead 14, features to limit the relative movement without damaging lead 14, or other useful structures.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An extendable and retractable electrical lead for providing electrical stimulation comprising:

an elongated lead body extending from a proximal portion to a distal portion;

one or more electrical contacts carried by the proximal portion of the lead body and configured to be coupled to an implantable neurostimulator;

one or more electrodes carried by the distal portion of the lead body configured to electrically communicate with the one or more electrical contacts to deliver neurostimulation therapy to a target treatment site based on a stimulation therapy provided by an implantable neurostimulator; and a protective sheath coaxially aligned with the lead body along a common axis and extending over part of a length of the lead body, the protective sheath is configured to slide relative to the lead body and the common axis between an extended state wherein the protective sheath does not cover the one or more electrodes, and a retracted state wherein the protective sheath covers the one or more electrodes, wherein the protective sheath comprises at least one flexible seal coupled to a distal end of the protective sheath and to the lead body, wherein in the extended state the flexible seal is extended, and further wherein in the retracted state the flexible seal is folded back on itself and drawn within an inner lumen of the protective sheath such that the seal is positioned between the protective sheath and the lead body, wherein the electrical lead is configured to be implanted in the extended state such that the protective sheath does not cover the one or more electrodes.

2. The extendable and retractable electrical lead of claim 1, wherein the protective sheath comprises an elongated tubular section, wherein in the retracted state, the tubular section is positioned over the one or more electrodes.

3. The extendable and retractable electrical lead of claim 2, wherein in each of the retracted state and the extended state, the tubular section is not positioned over the one or more electrical contacts.

4. The extendable and retractable electrical lead of claim 2, wherein the one flexible seal is coupled to a distal end of the tubular section.

5. The extendable and retractable electrical lead of claim 4, wherein the flexible seal has a first end coupled to the distal end of the tubular section and a second end coupled to the lead body.

6. The extendable and retractable electrical lead of claim 5, wherein in the extended state, the second end of the flexible seal is positioned distal relative to the first end, and wherein in the retracted state, the second end of the flexible seal is positioned proximal relative to the first end.

7. The extendable and retractable electrical lead of claim 4, wherein the flexible seal fluidically seals the distal end of the tubular section to the lead body.

8. The extendable and retractable electrical lead of claim 2, wherein the protective sheath comprises at least one sliding gasket coupled to a distal end of the tubular section, wherein the sliding gasket is configured to slide relative to the lead body.

9. The extendable and retractable electrical lead of claim 2, wherein at least one contacting surface between the tubular section and the lead body comprises a lubricious coating or surface treatment reducing friction between surfaces.

10. The extendable and retractable electrical lead of claim 1, wherein the protective sheath comprises at least one reinforcement material or design feature.

11. The extendable and retractable electrical lead of claim 1, wherein the protective sheath and the lead body are configured to transition between the retracted state and the extended state by manipulating the protective sheath and the lead body at the proximal portion of the retractable electrical lead.

12. The extendable and retractable electrical lead of claim 1, wherein a transition between the retracted state and the extended state is actuated by pneumatics, hydraulics, or wires.

13. The extendable and retractable electrical lead of claim 1, further comprising an anchoring device coupled to the protective sheath.

14. An extendable and retractable electrical lead for providing electrical stimulation comprising:

an elongated lead body extending from a proximal portion to a distal portion;

one or more electrical contacts carried by the proximal portion of the lead body and configured to be coupled to an implantable neurostimulator;

one or more electrodes carried by the distal portion of the lead body configured to electrically communicate with the one or more electrical contacts to deliver neurostimulation therapy to a target treatment site based on a stimulation therapy provided by an implantable neurostimulator; and a protective sheath coaxially aligned with the lead body along a common axis and extending over part of a length of the lead body, the protective sheath including an elongated tubular section and at least one flexible seal coupled to a distal end of the tubular section and to the lead body, wherein the protective sheath is configured to be slidable relative to the lead body and the common axis between an extended state and a retracted state, further wherein:

in the retracted state, the tubular section is positioned over the one or more electrodes, the tubular section is proximal to the one or more electrical contacts and not positioned over the one or more electrical contacts, the second end of the flexible seal is positioned proximal relative to the first end, and the flexible seal is folded back on itself and drawn within an inner lumen of the protective sheath such that the seal is positioned between the protective sheath and the lead body, and in the extended state, the second end of the flexible seal is positioned distal relative to the first end and the tubular section is not positioned over the one or more electrical contacts, and wherein the protective sheath and the lead body are configured to transition between the retracted state and the extended state by manipulating the protective sheath and the lead body at the proximal portion of the retractable electrical lead, wherein the electrical lead is configured to be implanted in the extended state such that the protective sheath does not cover the one or more electrodes.

* * * * *